United States Patent
Micic et al.

(10) Patent No.: US 11,199,477 B2
(45) Date of Patent: Dec. 14, 2021

(54) CULTIVATION AND SAMPLING DEVICE FOR PLANTS

(71) Applicant: Deutsche Saatveredelung AG, Lippstadt (DE)

(72) Inventors: Zeljko Micic, Salzkotten (DE); Simon Radtke, Soest (DE)

(73) Assignee: DEUTSCHE SAATVEREDELUNG AG, Lippstadt (DE)

( * ) Notice: Subject to any disclaimer, the term of this patent is extended or adjusted under 35 U.S.C. 154(b) by 172 days.

(21) Appl. No.: 16/293,185

(22) Filed: Mar. 5, 2019

(65) Prior Publication Data

US 2019/0195747 A1    Jun. 27, 2019

Related U.S. Application Data

(63) Continuation of application No. PCT/DE2017/100739, filed on Sep. 5, 2017.

(30) Foreign Application Priority Data

Sep. 5, 2016    (EP) .................................. 16187274

(51) Int. Cl.
*G01N 1/04* (2006.01)
*A01G 7/00* (2006.01)
(Continued)

(52) U.S. Cl.
CPC ................. *G01N 1/04* (2013.01); *A01G 3/00* (2013.01); *A01G 7/00* (2013.01); *A01G 9/028* (2013.01);
(Continued)

(58) Field of Classification Search
CPC ............... G01N 1/04; G01N 2001/288; G01N 2001/021; A01G 24/42; A01G 3/00;
(Continued)

(56) References Cited

U.S. PATENT DOCUMENTS 5,741,463 A * 4/1998 Sanadi ................. B01L 3/5025
422/527
5,846,493 A * 12/1998 Bankier .............. B01L 3/50255
422/535
(Continued)

FOREIGN PATENT DOCUMENTS

JP    2008118963 A * 5/2008 .......... B01L 3/50255
JP    2008118963 A    5/2008
(Continued)

OTHER PUBLICATIONS

International Search Report dated Jan. 5, 2018 in corresponding application PCT/DE2017/100739.
International Preliminary Report on Patentability dated Mar. 14, 2019 in corresponding application PCT/DE2017/100739.

*Primary Examiner* — Samuel P Siefke
*Assistant Examiner* — Tingchen Shi
(74) *Attorney, Agent, or Firm* — Muncy, Geissler, Olds & Lowe, P.C.

(57) ABSTRACT

A sampling device for plants having a lower section with a plurality of sample containers, an upper section with a plurality of cultivation containers, a cutter and a cutting tip, wherein a base opening is formed in each cultivation container and corresponds to a sample container opening of one of the sample containers, and wherein the cutter and cutting tip are arranged, when the sampling device is in a usage position, between the upper section and the lower section such that a part of a plant protruding out through the base opening of the cultivation container and in through the sample container opening into the sample container can be severed by the cutter and cutting tip.

11 Claims, 14 Drawing Sheets

(51) Int. Cl.
  *G01N 33/00*   (2006.01)
  *A01G 9/029*   (2018.01)
  *A01G 31/06*   (2006.01)
  *A01G 3/00*    (2006.01)
  *A01G 9/02*    (2018.01)
  *G01N 1/28*    (2006.01)
  *A01G 31/02*   (2006.01)
  *G01N 1/00*    (2006.01)

(52) U.S. Cl.
  CPC ............ *A01G 9/029* (2018.02); *A01G 31/06* (2013.01); *G01N 1/286* (2013.01); *G01N 33/0098* (2013.01); *A01G 31/02* (2013.01); *G01N 1/00* (2013.01); *G01N 2001/288* (2013.01); *G01N 2001/2873* (2013.01)

(58) Field of Classification Search
  CPC .......... A01G 31/02; A01G 31/06; A01G 7/00; A01G 9/028; A01G 9/029; A01G 9/0295
  See application file for complete search history.

(56)  References Cited

U.S. PATENT DOCUMENTS

| | | | |
|---|---|---|---|
| 6,054,100 A * | 4/2000 | Stanchfield | B01J 19/0046 422/534 |
| 7,749,451 B2 * | 7/2010 | West | B01L 3/50853 422/534 |
| 9,656,264 B2 | 5/2017 | Tortorella | |
| 2008/0131254 A1 * | 6/2008 | Cope | G01N 1/04 414/754 |
| 2013/0180171 A1 * | 7/2013 | Oldenburg | A01G 7/00 47/63 |

FOREIGN PATENT DOCUMENTS

| | | | |
|---|---|---|---|
| WO | WO-0119520 A1 * | 3/2001 | ......... B01L 3/50255 |
| WO | WO0119520 A1 | 3/2001 | |
| WO | WO-2012096568 A1 * | 7/2012 | ............ A01G 7/00 |
| WO | WO2012096568 A1 | 7/2012 | |
| WO | WO2012116932 A2 | 9/2012 | |

* cited by examiner

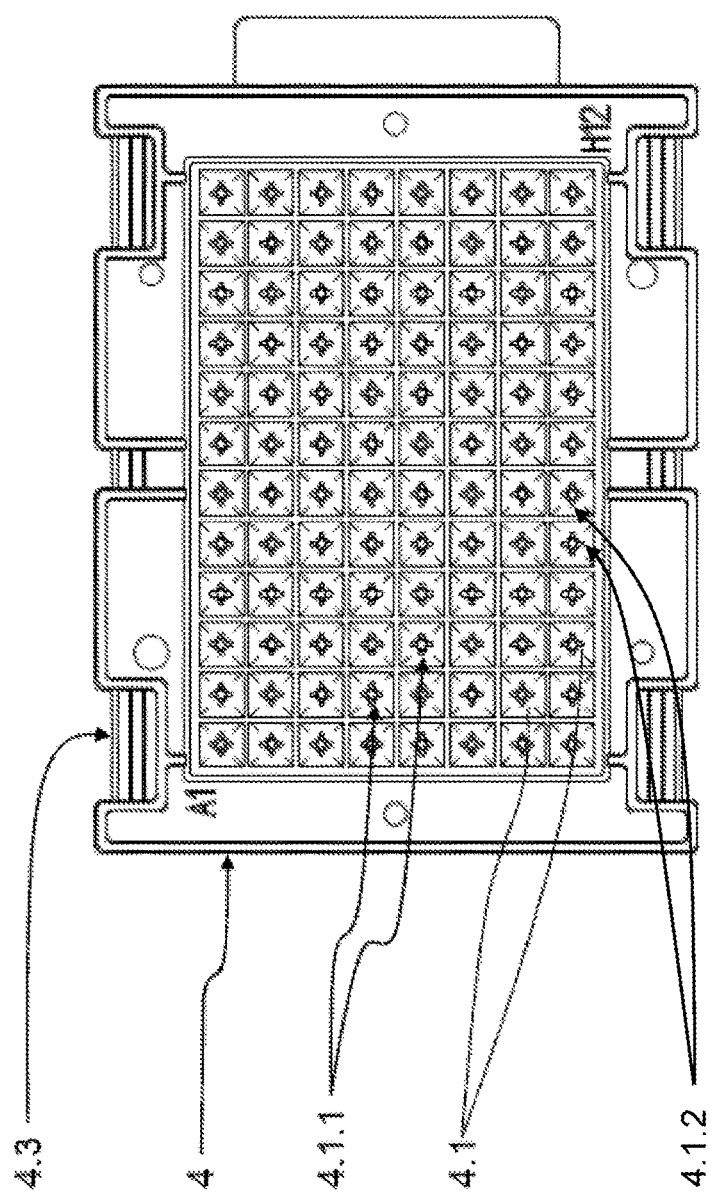

CULTIVATION AND SAMPLING DEVICE FOR PLANTS

This nonprovisional application is a continuation of International Application No. PCT/DE2017/100739, which was filed on Sep. 5, 2017, and which claims priority to European Patent Application No. 16187274.2, which was filed on Sep. 5, 2016, and which are both herein incorporated by reference.

BACKGROUND OF THE INVENTION

Field of the Invention

The present invention relates to a cultivation and sampling device for plants. The device according to the invention can be hereinafter referred to as a sampling device for the sake of simplicity.

Description of the Background Art

Generic sampling devices are already known and are used inter alia for phenotypic descriptions and genetic testing in the cultivation of crops. These are, for example, tongs by means of which tissue is punched out of plants. The punched plant parts, such as chlorophyll, are then placed in sample containers and are submitted for further laboratory testing.

SUMMARY OF THE INVENTION

It is therefore an object of the present invention to provide a sampling device, in which the amount of work in the description and/or testing and/or cultivation of plants is further reduced, and to make the cultivation of crops more efficient.

To achieve the object, the invention is characterized in that the sampling device comprises a lower section with a plurality of sample containers, an upper section with a plurality of cultivation containers, a cutter and a cutting plate, wherein in each cultivation container, a bottom opening is formed, which corresponds to a sample container opening of one of the sample containers, and wherein the cutter and the cutting plate are arranged in a position of use of the sampling device between the upper and lower sections such, that a plant part protruding out through the bottom opening of the cultivation container and through the sample container opening into the sample container can be severed by means of the cutter and the cutting plate.

The particular advantage of the invention is that a high amount of sampling can be done with much less manual labor. The plants can be grown in the individual cultivation containers. It may be advantageous if the cultivation containers have already been filled with the nutrients required for this purpose, for example, in a pre-assembly.

During plant development, the roots of the plants grow out through the bottom openings of the cultivation containers and through each corresponding sample container opening into the corresponding sample container. Sampling takes place by means of the cutter sliding along the cutting plate, wherein the roots of the plants are severed. Manual assignment of manually punched tissue samples to the individual sample containers is not required. This also reliably prevents faulty assignments.

The cutter and/or the cutting plate can be designed as a perforated plate. In this way, it is possible, for example, to assign each individual pair of cultivation containers on the one hand, and sample containers on the other, an individual cutter and/or an individual cutting plate. Undesired mixing of tissue samples (cross contamination) is thereby effectively prevented.

The cultivation containers with the bottom openings and the sample containers with the sample container openings can be uniformly spaced and/or arranged in a matrix-like and/or mosaic-like manner. For example, cutting holes in the manner of passage openings may be provided in a corresponding manner on the cutter and the cutting plate, uniformly spaced and/or in the manner of a matrix and/or a mosaic. The cultivation containers and/or the sample containers may be, for example, circular and/or a rectangular in cross section.

Generally, the cutting plate can be freely selectable according to type, material, shape, dimensioning and arrangement within wide suitable limits. Conveniently, the cutting plate is designed as a cover for the lower section. The cutting plate and/or the cutter can be made for example of plastic and/or of a ceramic material and/or of a metallic material. The cutter and the cutting plate can be made of the same material or of different materials.

The cutter can be laid flat against the cutting plate and/or is held relative to the same so that it can be moved longitudinally. For this purpose, the cutter and the cutting plate can have contact surfaces that face each other and are planar at least in sections.

A surface of the lower section facing the cutter and/or a surface of the upper section facing the cutter can be designed as a cutter guide. As a result, the cutter is safely guided between the cutter insert on the one hand, and the cutter guide formed in the aforementioned manner on the other. Accordingly, the quality of the cut is improved.

The type of mechanical connection between the individual components of the sampling device according to the invention is freely selectable within wide suitable limits. Advantageously, at least two components from the group upper section, cutter, cutting plate and lower section can be secured to one another by means of a clamping connection. As a result, a releasable connection between at least two components of the sampling device is realized in a structurally simple manner.

The design of the clamping connection and in particular the clamps in respect of shape, material, arrangement and number determines a mounting or clamping force during the cutting process. Optionally, the clamping connection may be modified for different crops.

The lower section and the cutting plate can be connected by means of at least one first clamp, and the upper section, the cutter and the lower section with the cutting plate clamped thereto can be connected by means of at least one second clamp. In this way, it is possible to only partially disassemble the sampling device during intended use or to make it available partially assembled in the course of production. This makes sense, for example, if the lower section fitted with the filled sample containers is to be transported for laboratory testing.

The upper section can have a base plate and an attachment which carries the cultivation containers, wherein the attachment and the base plate are releasably connected to one another in the position of use of the sampling device. As a result, it is possible, for example, to use attachments designed as pre-assembled parts, among other things as prefabricated parts preassembled with nutrients.

The bottom opening of each cultivation container of the attachment is surrounded on the outside by a tubular collar, wherein the collar in the position of use of the sampling device extends substantially to the end of the base plate facing away from the attachment. In this way, contact with the base plate of the upper section is effectively prevented.

A punch may additionally be provided. Pins rise from a base plate of the punch, which each may have a positioning head. The number of pins can be identical with the number of sample containers and thus with the number of cultivation containers. The punch is preferably made of metal. For example, the punch can be made of a plastic. The punch serves to reliably prevent cross contamination of the root samples when lifting the cutting plate from the lower section. For this purpose, after cutting the roots and removing the one-piece or multi-part upper section, annular, in particular circular sections are punched out of the cutting plate around the individual cutting holes with the punch and transferred into the interior of each associated sample container. For this purpose, the punch is brought into engagement with the cutting plate. In order to ensure and facilitate safe alignment of the punch with its pins to the cutting plate and the cutting holes, positioning heads can be provided on the individual pins which first enter into engagement with the cutting holes of the cutting plate when the punch approaches the cutting plate. In the further movement of the punch in the direction of the cutting plate, the pins of the punch come into contact with edges of the cutting holes of the cutting plate. The thickness of the cutting plate can be weakened at the edges of the cutting holes, so that in the further movement in the direction of the cutting plate, the punch breaks the predetermined breaking points of the cutting plate thus formed. In the described movement of the punch in the direction of the cutting plate, the individual pins of the punch have a corresponding dimensioning to reliably transfer the edges of the cutting holes with the cutting holes formed therein into the interior of each corresponding sample container. This allows for subsequent lifting of the cutting plate from the lower section, without root parts being pulled out from the individual sample containers of the lower section in an undesirable manner.

The grooves formed as drainage openings can embrace the cutting holes of the cutting plate at least sectionally and/or at the same time serve as predetermined breaking points for the punching operation.

Another development may provide a modified cutting plate. On the lower side of the modified cutting plate facing the lower section, drainage openings designed as grooves can be formed. Each of the drainage openings is assigned to exactly one sample container so as to effectively prevent unwanted cross contamination.

In the cultivation containers belonging to the inventive sampling device, plants are grown. For this purpose, the cultivation containers are filled with nutrients for plant growth. To store the required amount of water for growth, granules or the like may be incorporated in the cultivation containers. The cultivation containers are watered so as to soak the granules in water, which is then released from the granules to the plants. When watering, it may happen that an excess amount of water is added to the individual cultivation containers. This water cannot be absorbed by the granules; it runs through the bottom openings of the affected cultivation containers into their assigned sample containers. For further genetic testing, it is not harmful that there is water in the sample containers. However, it is undesirable that cultivation containers be flooded with water. Therefore, this development provides a modified cutting plate with drainage openings, such as grooves. The drainage openings are arranged on the bottom of the cutting plate such that water, which cannot be absorbed by the individual sample container, does not rise in an undesirable manner into the corresponding cultivation container, but rather passes through the sample container opening into the respective drainage opening and can drain via the bottom of the cutting plate without undesirably flowing into one of the other sample containers. In this way, waterlogging and any unwanted contaminations are effectively avoided.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 13 illustrates an exemplary embodiment of the sampling device according to the invention in a perspective exploded view in a partial view and FIG. 14 illustrates a fifth exemplary embodiment in a plan view in a partial view.

DETAILED DESCRIPTION

The figures show embodiments of the sampling device according to the invention that are different from each other. Only the features of the exemplary embodiments following the first exemplary embodiment that differ from the first exemplary embodiment will be explained. Otherwise, the exemplary embodiments are identical.

Figure 1:
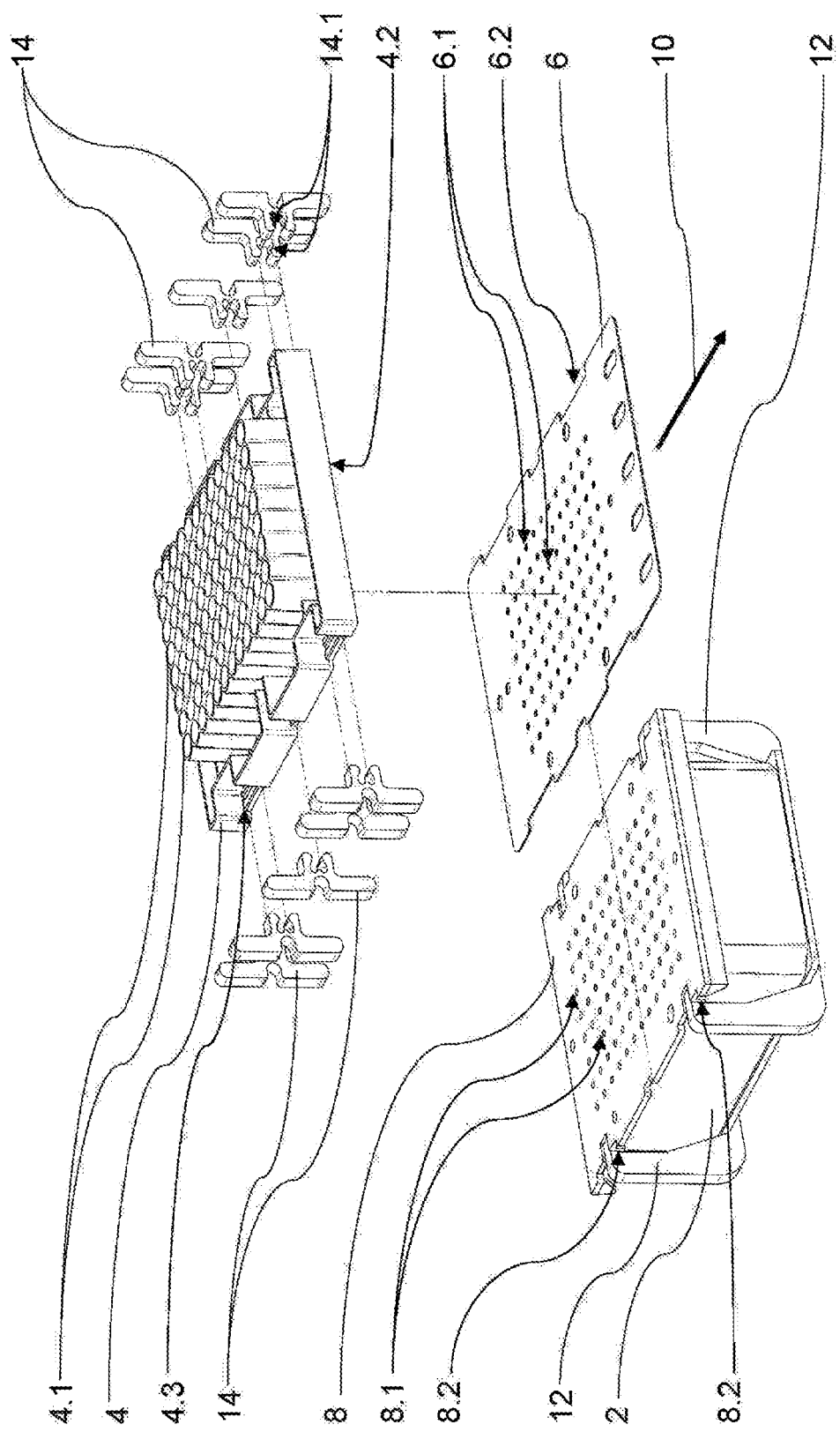
FIG. 1 illustrates an exemplary embodiment of an inventive sampling device in a first perspective exploded view.
Figure 2:
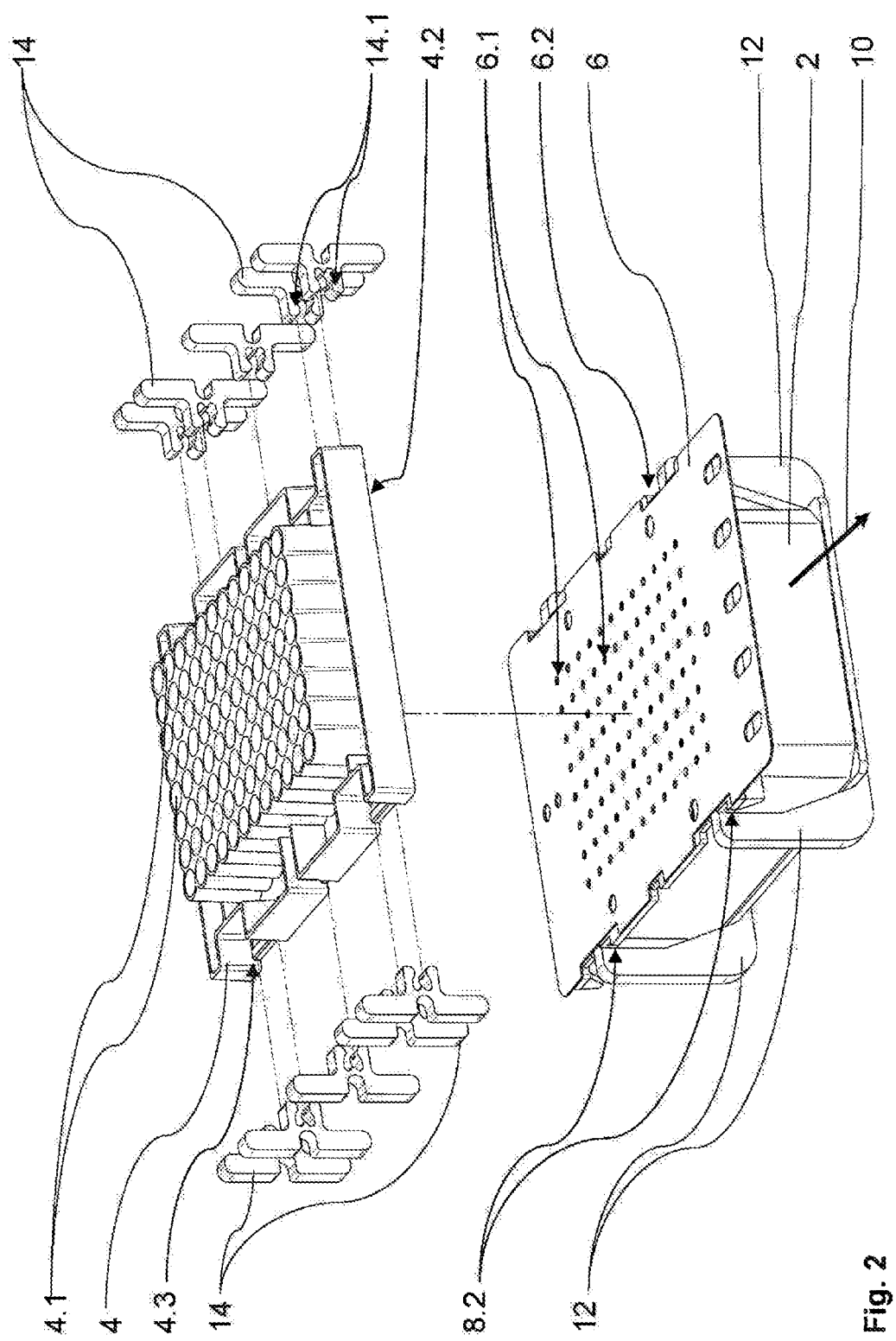
FIG. 2 illustrates the exemplary embodiment in a second perspective exploded view.
Figure 3:
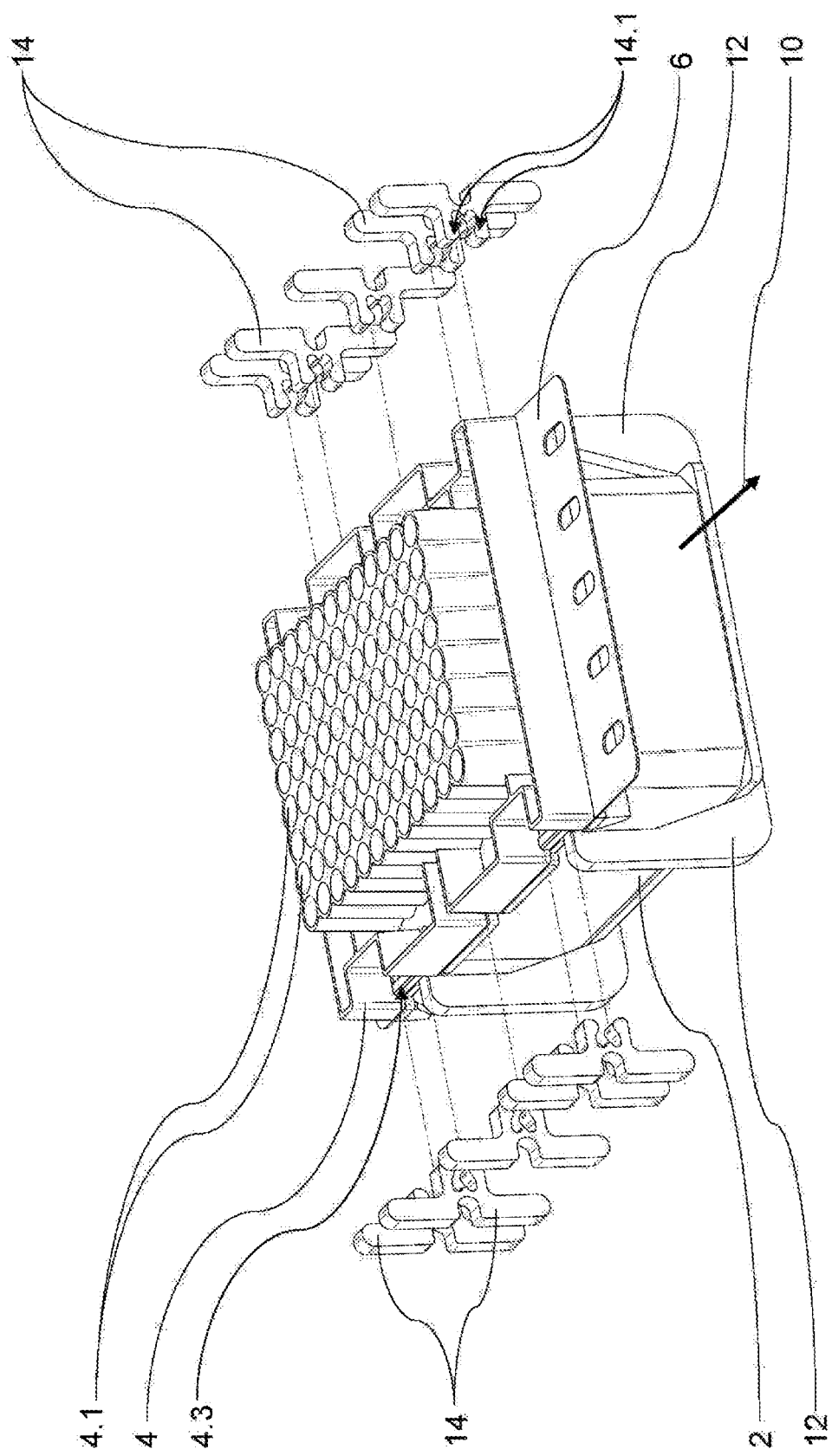
FIG. 3 illustrates the exemplary embodiment in a third perspective exploded view.

FIG. 1 shows an exemplary embodiment of a sampling device according to the invention in a perspective exploded view. The sampling device has a lower section 2 preferably at least partially made of plastic with a plurality of sample containers 2.1, which are particularly clearly recognizable in a perspective bottom view of the sampling device of FIG. 5.

Figure 6:
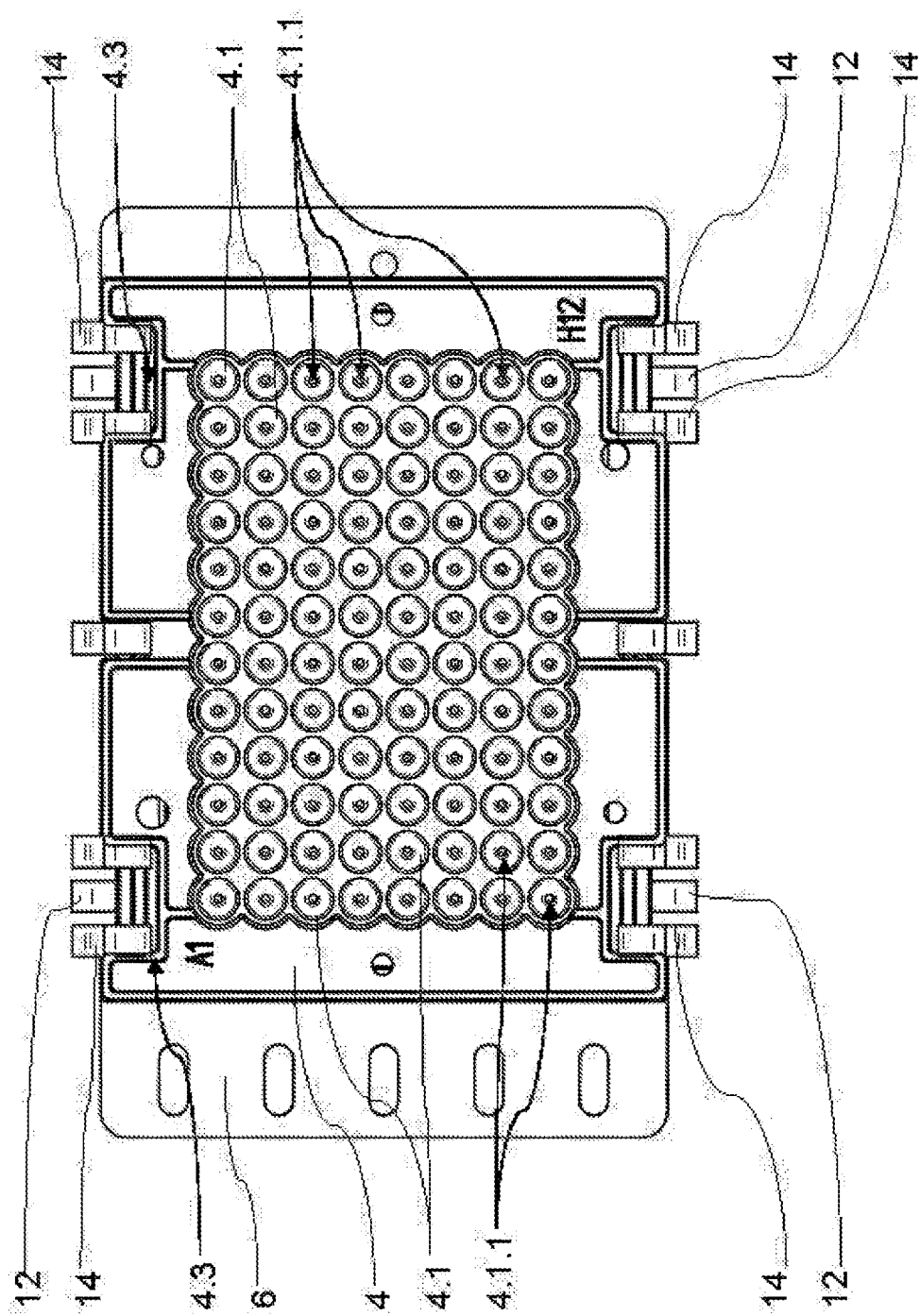
FIG. 6 illustrates the exemplary embodiment of the inventive sampling device in a plan view.

Furthermore, the sampling device has a plastic upper section 4 with a plurality of cultivation containers 4.1, a cutter 6 preferably made of plastic or metal, and a cutting plate 8 preferably made of plastic, wherein each cultivation container 4.1 has a bottom opening 4.1.1, which can be seen in FIG. 6. The sample containers 2.1 here are an integral part of the lower section 2, and the cultivation containers 4.1 are an integral part of the upper section 4. In the first exemplary embodiment of the invention, the lower section 2 and the upper section 4 are thus each formed in one piece.

Figure 4:
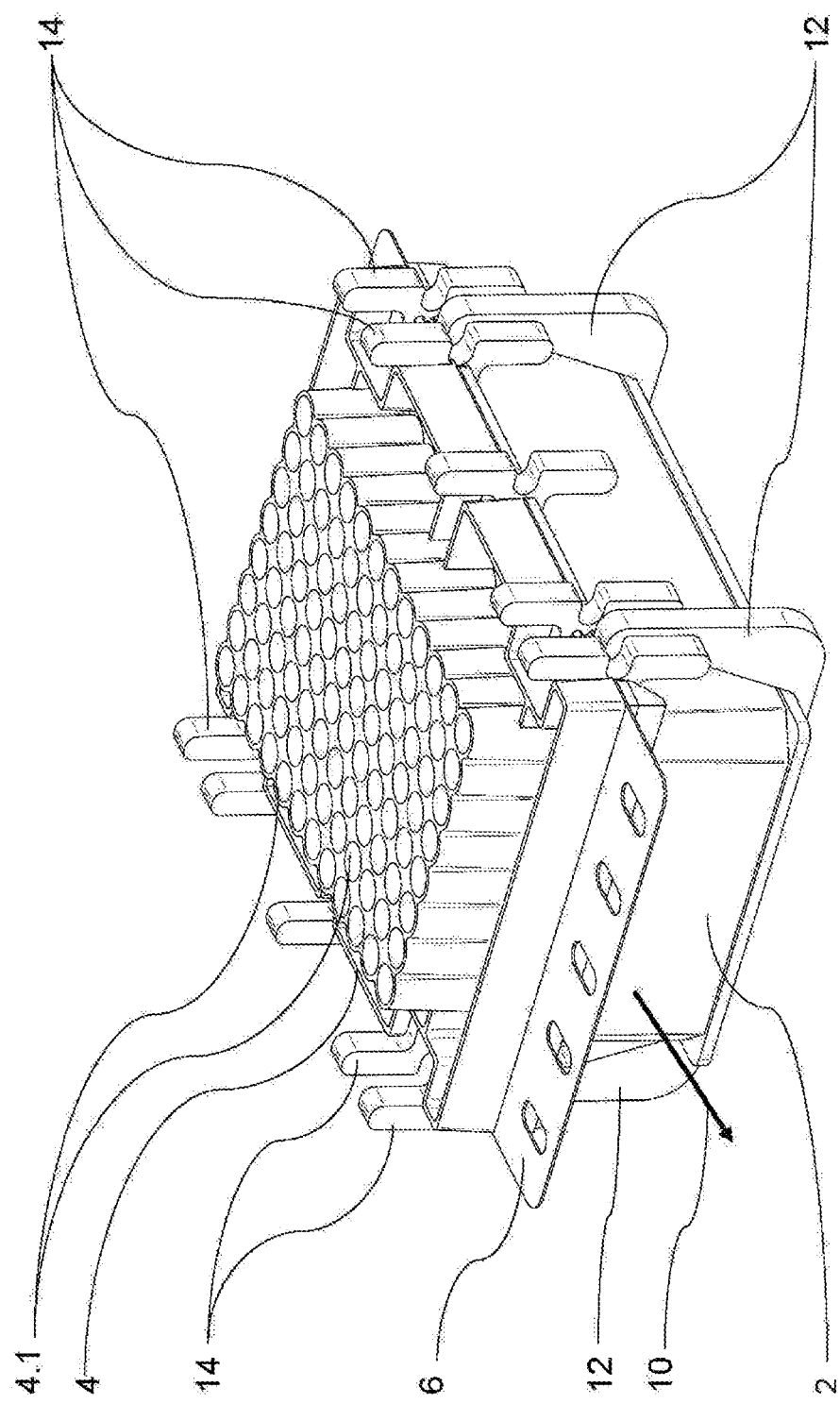
FIG. 4 illustrates the exemplary embodiment in a first perspective assembly view.
Figure 5:
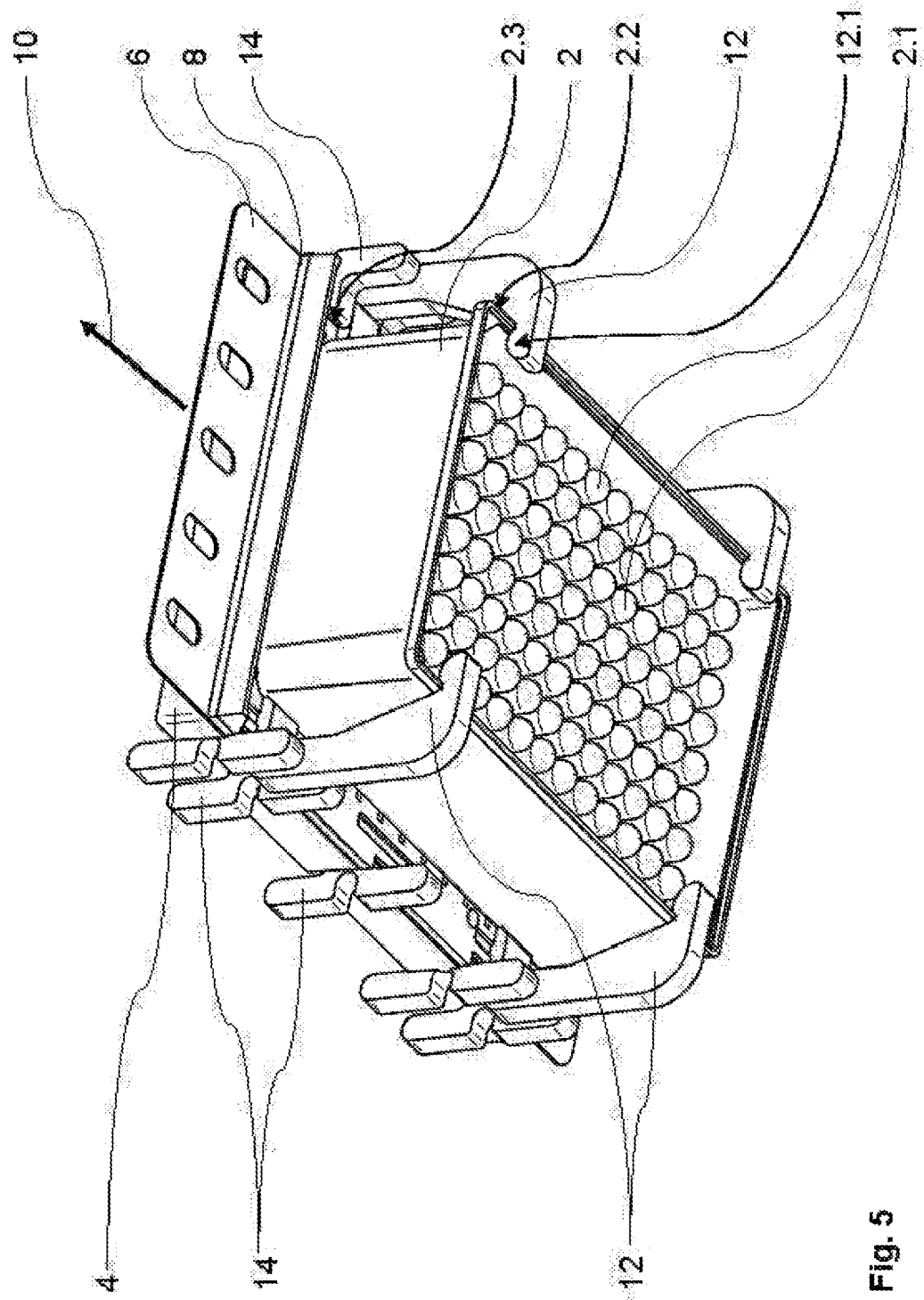
FIG. 5 illustrates the exemplary embodiment in a second perspective assembly view.

As is clear from the synopsis of the figures, each cultivation container 4.1 is assigned exactly one sample container 2.1 and each bottom opening 4.1.1 is assigned exactly one sample container opening in a position of use shown in FIGS. 4 to 6. The sample container openings are not explicitly shown because they are covered by the cutting plate 8.

The unambiguous assignment of exactly one cultivation container 4.1 to exactly one sample container 2.1 is useful because the sampling device here is provided in particular for the genetic testing of plants. For the success of such tests, it is important that there is no undesirable mixing (cross contamination) of the individual tissue samples (genotypes). This is ensured by the aforementioned embodiment of the sampling device.

In this case, the cultivation containers 4.1 were initially filled with nutrients for plant growth, not shown. In the individual cultivation containers 4.1, in each case a plant is grown during use of the sampling device according to the invention. In the further course of plant development, the roots of the plants, not shown, grow through the bottom openings 4.1.1 of the cultivation containers 4.1 and the sample container openings into the sample containers 2.1 of the lower section 2 which correspond to the individual cultivation containers 4.1.

In the position of use of the sampling device according to the invention as shown in FIGS. 4 to 6, the cutter 6 and the cutting plate 8 are arranged between the upper section 4 and the lower section 2 in such a way, that the roots projecting out through the bottom openings 4.1.1 of the cultivation containers 4.1 and projecting into the respective sample container 2.1 through the sample container openings can be severed by means of the cutter 6 and the cutting plate 8.

The cutter 6 and the cutting plate 8 are formed here as a perforated cutter 6 and a perforated cutting plate 8. The number of cutting holes 6.1, 8.1 formed in the two perforated plates 6, 8 is identical to the number of bottom openings 4.1.1 of the cultivation containers 4.1 and the number of sample container openings of the sample containers 2.1. The cultivation containers 4.1 and the sample containers 2.1 are preferably made of plastic.

In the position of use shown in FIGS. 4 to 6, the cutting holes 6.1, 8.1 formed on the cutter 6 and the cutting plate 8 are congruent with the bottom openings 4.1.1 and sample container openings corresponding thereto. Accordingly, the roots of the plants grown in the cultivation containers 4.1 can grow unhindered from the respective cultivation container 4.1 through the bottom openings 4.1.1, the cutting holes 6.1, 8.1 and the sample container openings into the respective sample container 2.1.

To cut through the roots, not shown, the cutter 6 is guided along the cutting plate 8 in the direction of the arrow (stroke direction 10) so that the roots are sheared off between the cutter 6 and the cutting plate 8, i.e., at the edges of the cutting holes 6.1, 8.1. In order to enable the movement of the cutter 6 parallel to the stroke direction 10, the cutter 6 has longitudinal recesses 6.2 on both its long sides, which will be explained in more detail below.

The cutting plate 8 on hand is designed as a removable cover 8 for the lower section 2, wherein the cutting plate 8 is releasably secured by means of first clamps 12 on the lower section 2. As is apparent in particular from FIGS. 1 and 5, the first clamps 12 embrace the lower section 2 and the cutting plate 8 in a clip-like manner and snap with locking projections 12.1 formed on the free ends of the first clamps 12 into correspondingly formed locking receptacles 8.2 of the cutting plate 8 and behind a locking collar 2.2 formed on the lower section 2.

In order for the first clamps 12 to not interfere with the movement of the cutter 6 along the cutting plate 8, the cutting plate 8 projects beyond the first clamps 12 in the position of use of the lower section 2 and the cutting plate 8.

Further, the assembly, which is formed from the lower section 2 and the cutting plate 8 attached thereto by means of the first clamps 12, is releasably connected to the cutter 6 and the upper section 4 by second clamps 14. For this purpose, the abovementioned components are precisely arranged one above the other and clamped with the second clamps 14. Analogous to the clamping connection between the lower section 2 and the cutting plate 8, the lower section 2 and the upper section 4 have locking receptacles 2.3 and 4.3, which enter a releasable locking connection with locking projections 14.1 formed at free ends of the second clamps 14 in a position of use shown in FIGS. 4 to 6.

To better guide the cutter 6 between the cutting plate 8 disposed on the lower section 2 and the upper section 4, sections of the base 4.2 of the upper section 4 facing the cutter 6 are formed level or planar as a cutter guide 4.2.

The inventive sampling device according to the first exemplary embodiment is designed such that the cutter 6 can be moved relative to the cutting plate 8 and parallel to the arrow 10, despite the clamping connections formed by the first and second clamps 12, 14 between the upper section 4, the cutter 6, the cutting plate 8 and the lower section 2.

This is possible, inter alia, because longitudinal recesses 6.2 are formed on the two long sides of the cutter 6. Accordingly, a movement of the cutter 6 parallel to the arrow 10 and in the required range of movement is not hindered by the second clamps 14. A stroke defined in the direction of the arrow 10 is limited by the length of the longitudinal recesses 6.2. The assignment of the cutting holes 6.1 of the cutter 6 to the cutting holes 8.1 of the cutting plate 8 on the one hand, the bottom openings 4.1.1 and the sample containers on the other hand, is preferably chosen such that in a first stroke end position of the cutter 6, the cutting holes 6.1, 8.1 are superimposed such that during the development of the plants, the plants can grow unhindered from the cultivation container 4.1 into the sample container 2.1, and that the roots of the plants are severed in the second stroke end position. The severing of the roots takes place without contamination as long as the cutter stroke is selected to be smaller than a distance of adjacent cutting holes 6.1, 8.1 specified in the actuating direction 10 of the cutter 6.

Figure 7:
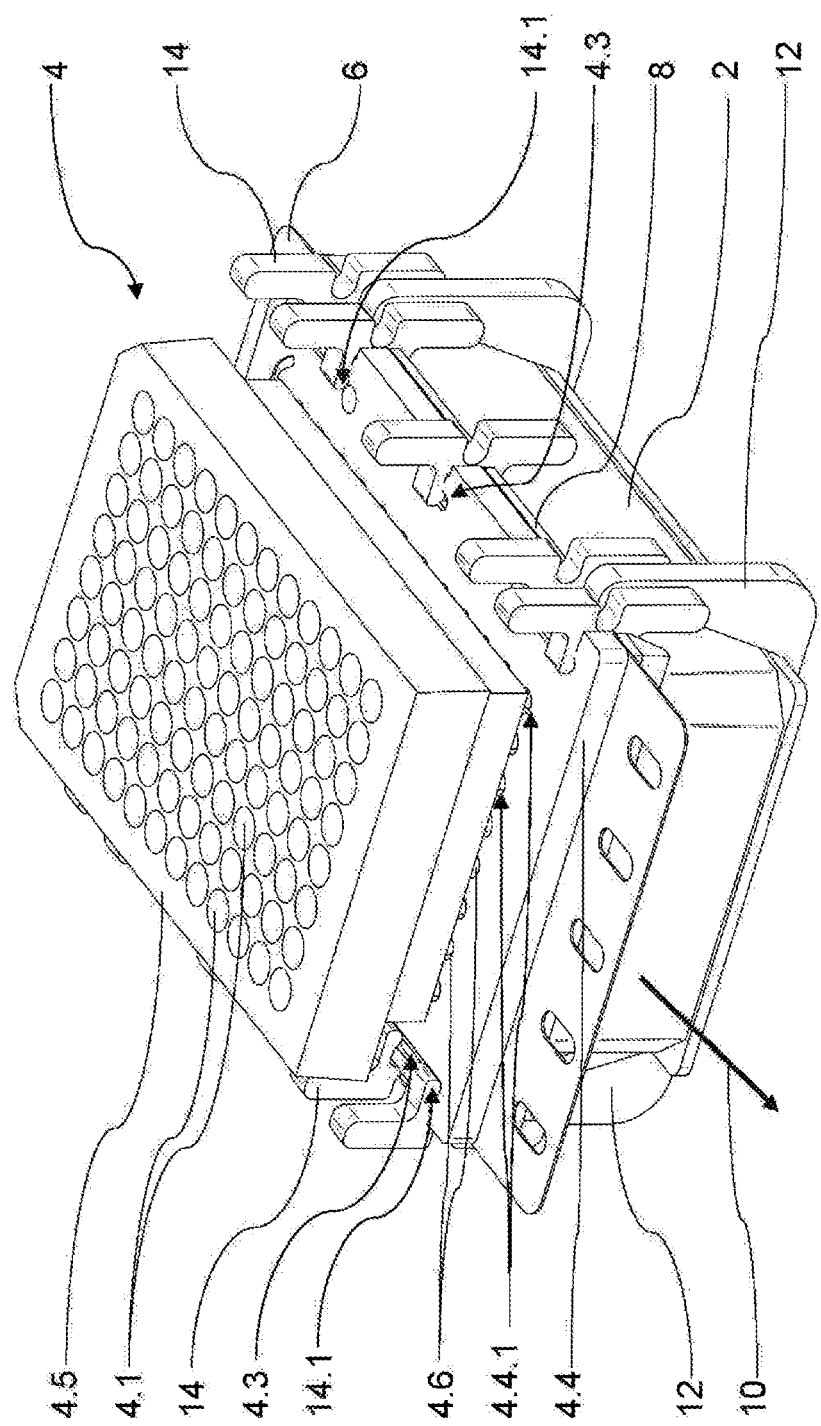
FIG. 7 illustrates an exemplary embodiment in a perspective assembly view corresponding to FIG. 4.

FIG. 7 shows a second exemplary embodiment of the sampling device according to the invention in an assembly position. In contrast to the first exemplary embodiment, the second exemplary embodiment has a two-part upper section 4. The upper section 4 here comprises a base plate 4.4 and an attachment 4.5 carrying the cultivation container 4.1, wherein the attachment 4.5 and the base plate 4.4 are releasably connected to one another in a position of use shown in FIG. 7.

The split of the upper section 4 serves to facilitate multiple use of the sampling device or so that the attachment 4.5 with the cultivation containers 4.1 can be used as a pre-assembled part.

In the present exemplary embodiment, the bottom opening of each cultivation container 4.1 of the attachment 4.5 is surrounded on the outside by a tubular collar 4.6, wherein the collar 4.6 in the position of use of the sampling device shown in FIG. 7 essentially extends as far as the end of the base plate 4.4 facing away from the attachment 4.5.

To secure the attachment 4.5 to the base plate 4.4, the attachment 4.5 is inserted with the tubular collar 4.6 into passage holes 4.4.1 formed on the base plate 4.4. The collars 4.6 and the corresponding passage holes 4.4.1 at the same time provide for positioning of the attachment 4.5 to the base plate 4.4.

The attachment 4.5 and the base plate 4.4 are preferably made of plastic.

In the position of use shown in FIG. 7, the assembly formed in this way of the base plate 4.4 and the attachment 4.5 comprising the cultivation containers 4.1 is releasably connected to the other components, namely the lower section 2 comprising the sample containers 2.1, the cutter 6 and the cutting plate 8, as already explained in regards to the first exemplary embodiment, by means of second clamps 14. Analogously to the first exemplary embodiment, the lower section 2 and the cutting plate 8 are also connected to each other in advance by means of first clamps 12.

In order to sever the roots projecting into the sample container 2.1, the cutter 6 in both exemplary embodiments can be moved both manually and by means of a motor drive along the cutting plate 8. The skilled person will take the appropriate measures according to the application.

A third exemplary embodiment of the teaching according to the invention is explained with reference to FIGS. 8 to 11.

Figure 8:
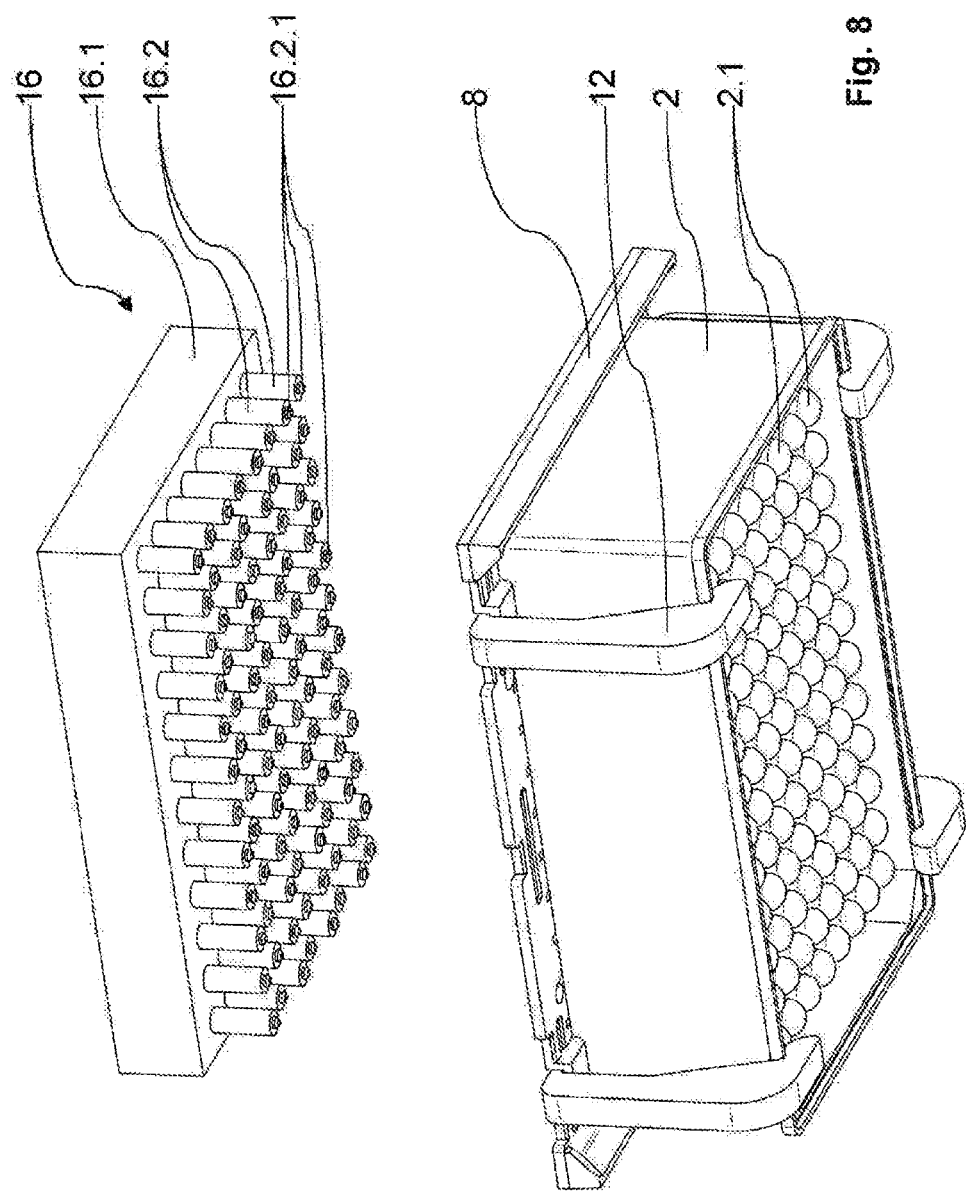
FIG. 8 illustrates an exemplary embodiment in a first perspective exploded view in a partial view.

FIG. 8 shows the third exemplary embodiment in an exploded perspective view in a partial view. Shown is the assembly of the lower section 2 with the sample containers 2.1, the first clamps 12 and the cutting plate 8. The lower section 2 with the sample containers 2.1 and the first clamps 12 as well as the components of the sampling device, not shown, such as the upper section 4 and the cutter 6, may be formed analogously to the first or the second exemplary embodiment.

In contrast to the first and the second exemplary embodiment, the sampling device of the third exemplary embodiment additionally has a further component, namely a punch 16. Pins 16.2 rise from a base plate 16.1 of the punch 16, each having a positioning head 16.2.1. The number of pins 16.2 is identical with the number of sample containers 2.1 and thus with the number of cultivation containers not shown here. The punch 16 is preferably made of a metallic material or plastic.

The punch 16 serves to reliably avoid cross contamination of the root samples when the cutting plate 8 is lifted off. To this end, after cutting the roots and removing the one-piece or two-piece upper section, not shown, circular sections are punched out of the cutting plate 8 around the individual cutting holes and transferred into the interior of each associated sample container 2.1 by means of the punch 16, also not shown here.

Figure 9:
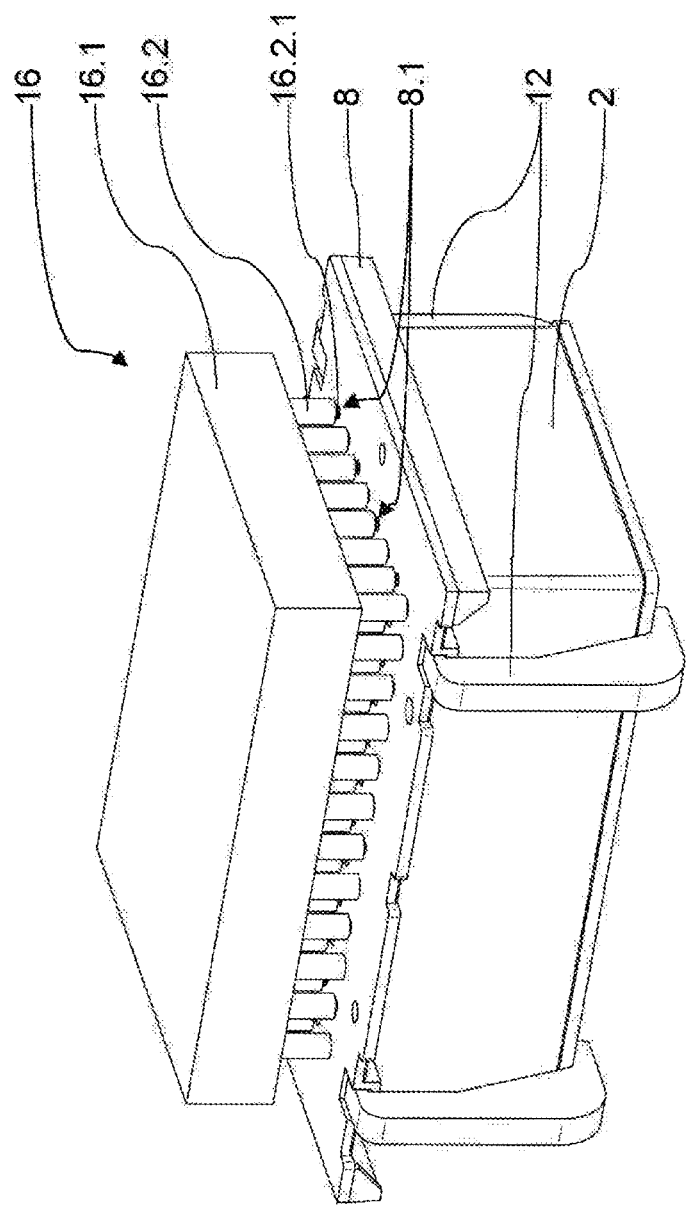
FIG. 9 illustrates the exemplary embodiment in a second perspective exploded view in a partial view.

As shown in FIG. 9, the punch 16 is brought into engagement with the cutting plate 8 for this purpose. In order to ensure and facilitate reliable alignment of the punch 16 with its pins 16.2 relative to the cutting plate 8 and the cutting holes 8.1, initially the positioning heads 16.2.1 formed on the pins 16.2 are brought into engagement with the cutting holes 8.1 of the cutting plate 8 when the punch 16 approaches the cutting plate 8. During the further movement of the punch 16 in the direction of the cutting plate 8, the pins 16.2 of the punch 16 come into contact with the edges of the cutting holes 8.1 of the cutting plate 8.

Figure 10:
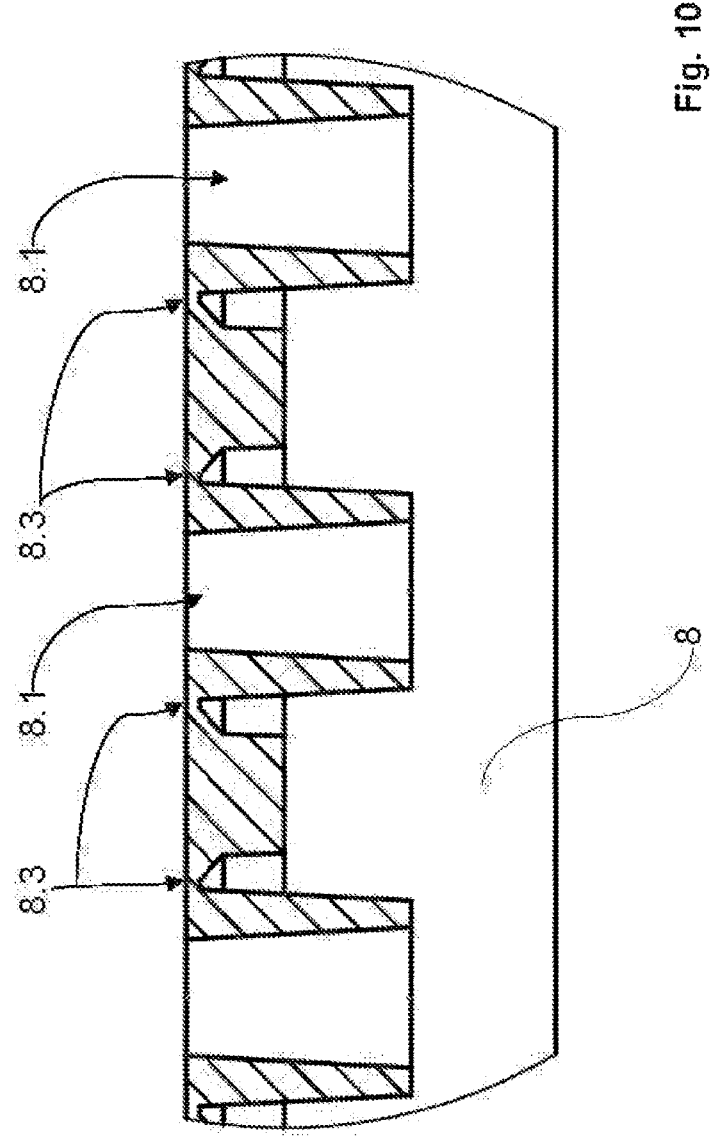
FIG. 10 illustrates the exemplary embodiment in a detailed view in the region of the cutting plate in a sectioned, partial view.

See FIG. 10, which shows a detail of the sampling device according to the third embodiment in the area of the cutting plate 8. Clearly illustrated are the edges 8.3, which surround the cutting holes 8.1 of the cutting plate 8. The thickness of the cutting plate 8 is weakened at the edges 8.3, so that the punch, not shown here, breaks the predetermined breaking points of the cutting plate 8 thus formed in the further movement in the direction of the cutting plate 8. During movement in the direction of the cutting plate 8 in the image plane of FIG. 10, the punch 16 is lowered manually or driven by a motor from above onto the cutting plate 8.

Figure 11:
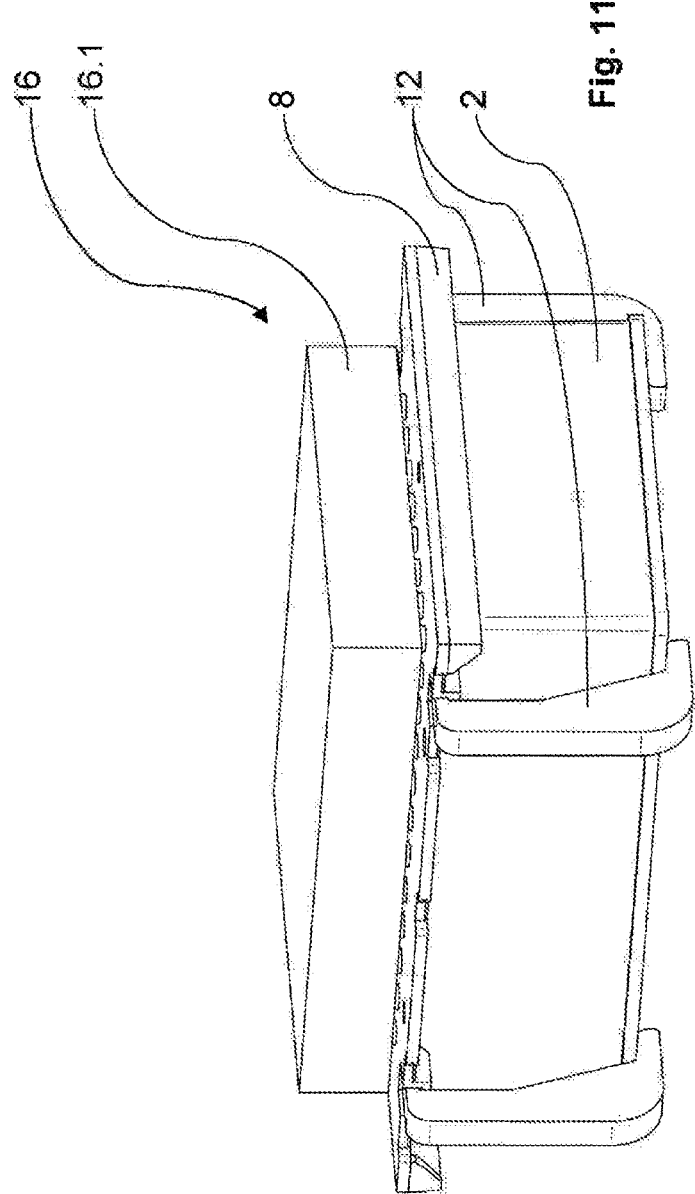
FIG. 11 illustrates the exemplary embodiment in a first perspective engagement view in a partial view.

The individual pins of the punch have a corresponding dimensioning to reliably transfer the edges 8.3 of the cutting plate 8 with the cutting holes 8.1 formed therein during the described movement of the punch, in the direction of the cutting plate 8 into the interior of the respective corresponding sample container, and to hold it in the sample container in order to effectively prevent undesired removal of root samples from the sample containers during removal of the cutting plate 8 from the lower section and thus from the sample containers. The lower section and the sample containers are also not shown in FIG. 10. FIG. 11 shows the punch 16 in the end position, in which the punch 16 rests with its base plate 16.1 on the cutting plate 8. For the sake of clarity, the base plate 16.1 in FIG. 11 is not shown completely lowered to the cutting plate 8.

Figure 12:
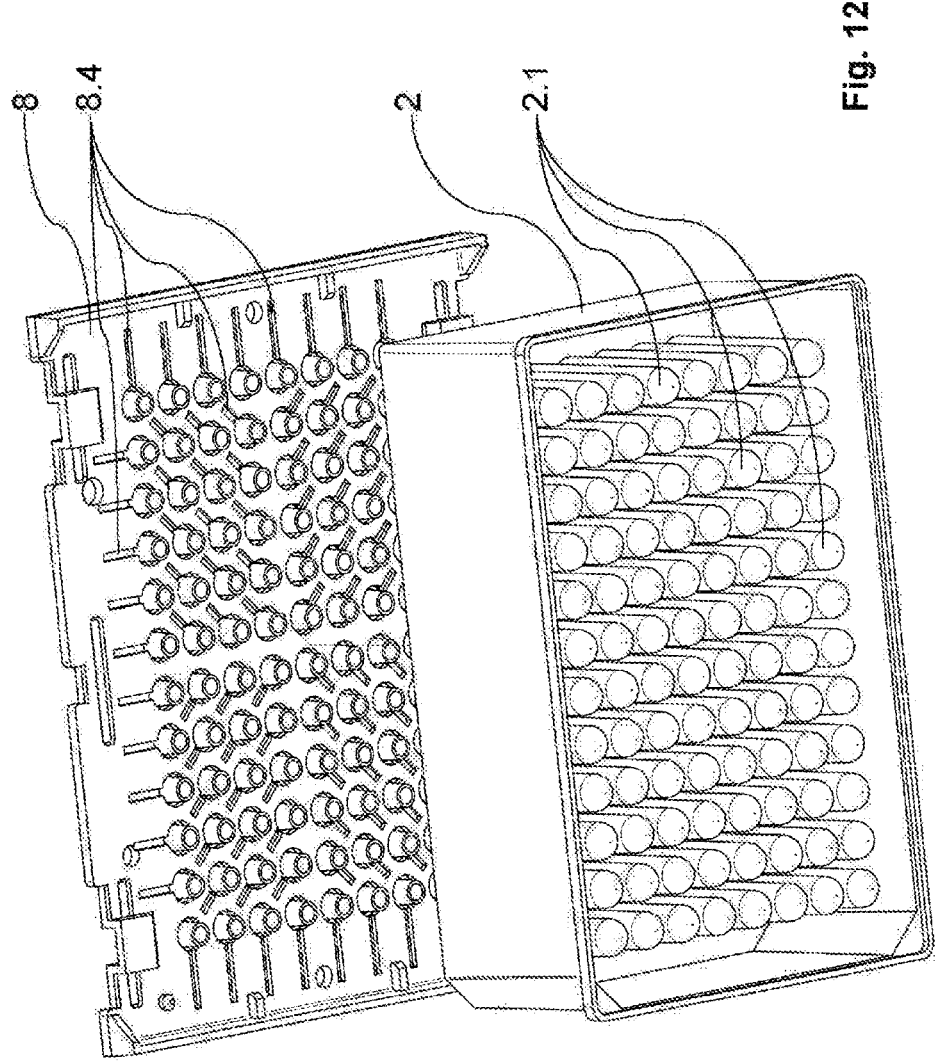
FIG. 12 illustrates an exemplary embodiment in a first perspective exploded view in a partial view.

FIG. 12 further shows a fourth exemplary embodiment. Shown is the lower section 2 with the sample containers 2.1 and the cutting plate 8 in a perspective bottom view. The lower section 2 with the sample containers 2.1 as well as the components of the sampling device, not shown, such as the upper section 4 and the cutter 6, may be formed analogously to the first or the second or the third exemplary embodiment.

In contrast to the already explained exemplary embodiments, the sampling device of the fourth exemplary embodiment has a modified cutting plate 8. As can be seen from FIG. 12, drainage openings 8.4 designed as grooves are formed in the bottom of the cutting plate 8. In the assembly position of the lower section 2 and cutting plate 8, not shown, each of the drainage openings 8.4 is assigned to exactly one sample container 2.1, so as to effectively prevent unwanted cross contamination.

As already explained in reference to the first exemplary embodiment, plants are grown in the cultivation containers, not shown in FIG. 12. For this purpose, the cultivation containers are filled with nutrients for plant growth. In order to store the required amount of water for growth, granules or the like may be added to the cultivation containers. The cultivation containers are watered so as to soak the granules with water, which is then released from the granules to the plants. When watering, it may happen that an excess amount of water is supplied to the individual cultivation containers. This water cannot be absorbed by the granules; it runs through the bottom openings of the affected cultivation containers into the sample containers assigned thereto.

For further, in particular genetic testing, it is not harmful that there is water in the sample containers 2.1. However, it is not desired that the cultivation containers are flooded with water. Therefore, in the fourth exemplary embodiment, a drainage opening 8.4 designed as a groove is provided for each sample container 2.1. The grooves 8.4 are arranged on the bottom of the cutting plate 8 such that water, which cannot be absorbed by the individual sample container 2.1, does not rise in an undesirable manner into the corresponding cultivation container, but rather passes through the sample container opening, not shown, into the respective groove 8.4 and can drain through the bottom of the cutting plate 8 without flowing into one of the other sample containers 2.1 in an undesirable manner. In this way, waterlogging is effectively avoided.

Figure 13:
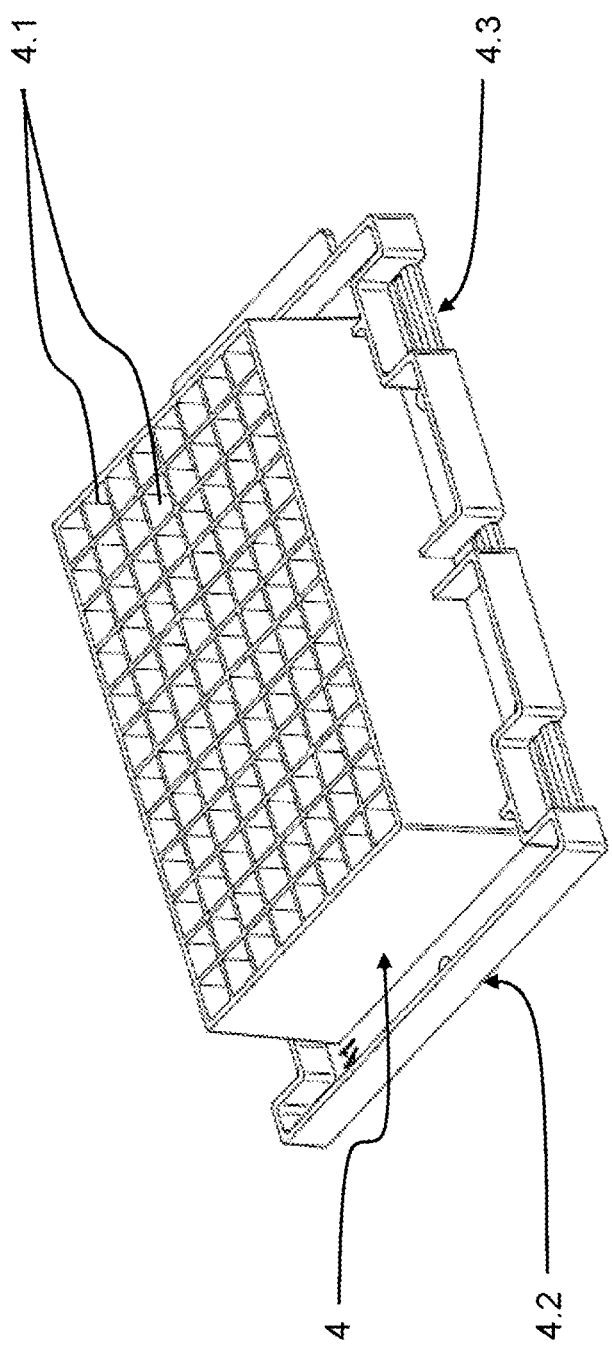

With reference to FIGS. 13 and 14, a fifth exemplary embodiment of the inventive teaching is explained. FIG. 13 shows the fifth exemplary embodiment in a perspective exploded view in a partial view. Shown is the upper section 4 with the cultivation containers 4.1, which are provided in an 8×12 matrix-like arrangement. According to the fifth exemplary embodiment, unlike previously, the cultivation containers 4.1 are rectangular in cross section. The rectangular cross section of the cultivation containers 4.1 provides a very good use of space, i.e., with an unaltered size of the upper section 4, the volume of the cultivation containers 4.1 can be increased.

The bottom openings 4.1.1 provided on the upper section 4 for each cultivation container 4.1 are surrounded in the circumferential direction by a plurality of tabs 4.1.2 pointing away from the lower section 2 of the sampling device as seen in the assembly position. The tabs 4.1.2 are spaced and arranged such that a blockage or obstruction of the bottom opening 4.1.1 by the nutrients is counteracted and that at the same time it can be ensured, that in the cultivation phase the roots can develop into the lower section through the bottom openings 4.1.1.

Of course, the upper section 4 can also be formed in two parts in the rectangular embodiment of the cultivation container 4.1 according to the fifth exemplary embodiment. Analogous to the realization of the inventive sampling device according to FIG. 7, the upper section 4 then comprises the base plate 4.4 and the attachment 4.5 with the cultivation containers 4.1 that are rectangular in cross section.

The invention is not limited to the aforementioned exemplary embodiments.

In order to be able to reliably align the individual components of the sampling device, for example lower section, upper section, cutter and cutting plate, with less of a burden in terms of monitoring, the components can have at least partially mutually corresponding positioning means even if the upper section is not split into two parts.

The positioning means may further be designed as coding, by which faulty mounting of the components of the inventive sampling device is effectively prevented by simple means.

In the mentioned exemplary embodiments, the sample containers of the lower section and the cultivation containers of the upper section are each an integral part of the lower section or the upper section. However, this is not mandatory. For example, it can also be provided that the sample containers and/or the cultivation containers are at least partially formed as a separate component.

The sampling device according to the invention can be designed both for single use and for repeated use. While the first embodiment is more suitable for use as a disposable sampling device, the second embodiment is better suited for multiple use.

In contrast to the exemplary embodiments, it would be fundamentally conceivable that a cultivation container with its bottom opening does not necessarily correspond exactly to a sample container and its sample container opening. It would also be possible for a cultivation container with its bottom opening to be associated with a plurality of sample containers and their sample container openings. As a result, the same plant material can be submitted for different tests.

The cutter does not necessarily have to be designed as a perforated plate. It is also conceivable that, for example, only the cutting plate is formed as a perforated plate and the cutter is otherwise suitably selected by the subject matter expert according to the individual case in respect of type, material, shape, dimensioning and arrangement.

For example, in addition to other suitable materials, cutters made of hardened tool steel, alloyed tool steel, hard metal, plastic or even cutting ceramics would be possible. The same applies to the material of the cutting plate.

In the two exemplary embodiments, in the position of use of the inventive sampling device, the second clamps 14 interact, inter alia, with locking receptacles 2.3 formed on the lower section 2. However, since the lower section 2 and the cutting plate 8 are releasably connected with each other by first clamps 12, it would also be conceivable that the second clamps cooperate with locking receptacles formed on the cutting plate.

The invention being thus described, it will be obvious that the same may be varied in many ways. Such variations are not to be regarded as a departure from the spirit and scope of the invention, and all such modifications as would be obvious to one skilled in the art are to be included within the scope of the following claims

What is claimed is:

1. A sampling device for plants comprising:
   a lower section with a plurality of sample containers;
   an upper section with a plurality of cultivation containers;
   a cutter; and
   a cutting plate,
   wherein, in each of the plurality of cultivation containers, a bottom opening is formed, which corresponds to a respective sample container opening of each of the plurality of sample containers,
   wherein, each of the plurality of cultivation containers is assigned exactly one of the plurality of sample containers and each bottom opening of the plurality of cultivation containers is assigned exactly one sample container opening of the plurality of sample containers,
   wherein the cutting plate forms a cover for the lower section,
   wherein the cutter and the cutting plate are each formed as a perforated plate with cutting holes,
   wherein a surface of the upper section that faces the cutter is formed as a cutter guide,
   wherein the cutter has two long sides with longitudinal recesses,
   wherein, the cutter and the cutting plate are arranged between the upper section and the lower section, such that plant roots protruding out through the bottom opening of each of the plurality of cultivation containers and protruding through the sample container opening of each of the plurality of sample containers is severed via the cutter and the cutting plate,
   wherein the cutter is laid flat against the cutting plate and is slidable relative to the cutting plate so that the cutter is moved longitudinally with a cutting stroke in an actuating direction from a first end position to a second end position, wherein the cutting stroke is limited by a length of the longitudinal recesses and is smaller than a distance between adjacent cutting holes in the actuating direction of the cutter, and wherein, in the first end position of the cutter, the cutting holes of the cutter and the cutting plate respectively correspond to the sample container opening of each of the plurality of sample containers and the bottom opening of each of the plurality of cultivation containers, such that the plant roots protrude through the cutting holes of the cutter and the cutting plate and wherein in the second end position of the cutter, the plant roots are severed via the cutter.

2. The sampling device according to claim 1, wherein at least two components from the group consisting of the upper section, the cutter, the cutting plate, and the lower section are fastened to each other by a clamping connection.

3. The sampling device according to claim 1, wherein the lower section and the cutting plate are interconnected by at least one first clamp and wherein the upper section, the cutter and the lower section, with the cutting plate already interconnected thereto, are interconnected by at least one second clamp.

4. The sampling device according to claim 3, wherein at least one component from the group consisting of the upper section, the lower section and the cutting plate has a locking element associated with the at least one first clamp and/or the at least one second clamp, wherein the locking element is a locking receptacle or a locking collar.

5. The sampling device according to claim 1, wherein the upper section includes a base plate and an attachment carrying the plurality of cultivation containers, wherein the attachment and the base plate are releasably connected with one another and wherein the base plate is arranged between the cutter and the attachment.

6. The sampling device according to claim 5, wherein the bottom opening of each of the plurality of cultivation containers of the attachment is surrounded on the outside by a tubular collar, the collar extending toward the base plate.

7. The sampling device according to claim 1, wherein at least individual components of the lower section and/or the upper section and/or the cutter and/or the clamps are made of plastic, and wherein the sample containers and/or the cultivation containers and/or the base plate are made of plastic.

8. The sampling device according to claim 3, wherein a first end of the at least one first clamp is attached to a locking collar of the lower section and a second end of the at least one first clamp is attached to a locking receptacle of the cutting plate, and wherein a first end of the at least one second clamp is attached to a locking receptacle of the lower section and a second end of the at least one second clamp is attached to a locking receptacle of the upper section.

9. The sampling device according to claim 8, wherein the cutter is plate-shaped, and wherein the longitudinal recesses of the cutter are provided at positions that correspond to the locking receptacle of the lower section and the locking receptacle of the upper section, such that the at least one second clamp does not hinder the cutting stroke of the cutter when the cutter slides to sever the plant roots.

10. The sampling device according to claim 6, wherein the base plate is provided with a plurality of passage holes that correspond to the tubular collar of each of the plurality of cultivation containers, such that the tubular collar of each of the plurality of cultivation containers is inserted into a respective one of the passage holes.

11. The sampling device according to claim 1, wherein the upper section, the lower section and the cutting plate are stationarily fastened to one another and wherein the cutter is slidably connected to the upper section and the cutting plate, such that the cutter is slidable with respect to the upper section and the cutting plate to sever the plant roots.

\* \* \* \* \*